United States Patent [19]

Boden et al.

[11] 4,339,344

[45] * Jul. 13, 1982

[54] USE OF MIXTURE OF ALIPHATIC $C_{10}$-BRANCHED OLEFINS IN AUGMENTING OR ENHANCING THE AROMA OF PERFUMES AND/OR PERFUMED ARTICLES

[75] Inventors: Richard M. Boden, Monmouth Beach; Lambert Dekker, Wyckoff; Frederick L. Schmitt, Holmdel, all of N.J.; Augustinus G. Van Loveren, Rye, N.Y.

[73] Assignee: International Flavors & Fragrances Inc., New York, N.Y.

[*] Notice: The portion of the term of this patent subsequent to Sep. 1, 1998, has been disclaimed.

[21] Appl. No.: 267,047

[22] Filed: May 28, 1981

Related U.S. Application Data

[60] Division of Ser. No. 188,576, Sep. 18, 1980, Pat. No. 4,303,555, which is a continuation-in-part of Ser. No. 160,788, Jun. 19, 1980, Pat. No. 4,287,084.

[51] Int. Cl.$^3$ .................. C11D 7/54; C11D 3/395; C11D 3/50

[52] U.S. Cl. .................. 252/187.24; 252/95; 252/99; 252/174.11; 252/522 R; 8/108 R; 8/108 A; 252/187.25; 252/187.27; 252/187.28; 252/186.21

[58] Field of Search .......... 252/187 H, 95, 99, 174.11, 252/522 R; 8/108 A, 108 R

[56] References Cited

U.S. PATENT DOCUMENTS

| | | | |
|---|---|---|---|
| 3,684,722 | 8/1972 | Hynam et al. | 252/187 H |
| 4,113,645 | 9/1978 | DeSimone | 252/187 H |
| 4,123,377 | 10/1978 | Davey et al. | 252/187 H |
| 4,208,297 | 6/1980 | Light et al. | 252/522 R |

*Primary Examiner*—Irwin Gluck
*Attorney, Agent, or Firm*—Arthur L. Liberman

[57] ABSTRACT

Described are methods for augmenting or enhancing the aroma of perfumes and perfumed articles by adding thereto perfume aroma augmenting or enhancing quantities of $C_{10}$-branched olefin mixtures produced by dimerizing isoamylene, (2-methyl-2-butene) as well as perfume compositions, colognes and perfumed articles including solid or liquid anionic, cationic, nonionic or zwitterionic detergents, fabric softener compositions, hair preparations and deodorant compositions as will as bleaching compositions containing same.

1 Claim, 10 Drawing Figures

FIG.1D

GLC PROFILE FOR EXAMPLE I.
CRUDE PRODUCT

FIG.1E

GLC PROFILE FOR EXAMPLE I.
DISTILLATION PRODUCT

FIG. 2A
NMR SPECTRUM FOR PEAK 1 OF EXAMPLE I, OF GLC OF FIG. 1E

FIG. 2B
IR SPECTRUM FOR EXAMPLE I, PEAK 1 OF GLC OF FIG. 1E

FIG. 3A

NMR SPECTRUM FOR EXAMPLE I, PEAK 2 OF GLC OF FIG. IE

IR SPECTRUM FOR EXAMPLE I PEAK 2 OF GLC OF FIG. IE

FIG. 3B

USE OF MIXTURE OF ALIPHATIC C₁₀-BRANCHED OLEFINS IN AUGMENTING OR ENHANCING THE AROMA OF PERFUMES AND/OR PERFUMED ARTICLES

This is a divisional of application Ser. No. 188,576, filed Sept. 18, 1980 now U.S. Pat. No. 4,303,555 which, in turn, is a continuation-in-part of Application for United States Letters Patent, Ser. No. 160,788 filed on June 19, 1980, now U.S. Pat. No. 4,287,084.

BACKGROUND OF THE INVENTION

The instant invention provides mixtures of $C_{10}$ branched chain olefins which are used to augment or enhance the aroma of perfume compositions, colognes and perfumed articles.

Chemical compounds which can provide a woody, piney and herbaceous aroma are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

Aliphatic hydrocarbons are well known in the art of perfumery, e.g. myrcene, 2-methyl-6-methylene-2,7-octadiene, a constituent of lemon grass oil. Also found in lemon oil as well as in Bergamot oil, according to Gildemeister and Hoffmann, (Die Atherischen Ole, 3rd edition, Volume 1, page 301) is octylene, a long chain olefin containing eight carbon atoms.

Arctander, "Perfume and Flavor Chemicals, (Aroma Chemicals)", 1969, Vol. I, at monograph 974, discloses the use of "di-isoprene" in perfumery. Arctander states that di-isoprene is a mixture of 2,6-dimethyl-2,6-octadiene; 2,7-dimethyl-2,6-octadiene; and 3,6-dimethyl-2,6-octadiene. Arctander states that this material has a sweet, diffusive, somewhat "gassy" odor and, overall, is of very "little interest to the perfumer." At monograph 1074, Arctander discloses "dipentene" having a use in perfumery and indicates that this "dipentene" is 1-methyl-4-iso-propenyl-1-cyclohexene and indicates that it is useful in perfumery as a "lift" in citrusy fragrances and in the reconstruction of many essential oils such as Bergamot, Lime and Lemon.

Nothing in the prior art discloses the use of diisoamylenes defined according to the generic structure:

wherein $R_1$, $R_2$, $R_3$, $R_4$ and $R_5$ represent hydrogen or methyl with the provisos that (i) at least one of $R_1$ and $R_2$ represents methyl (ii) at least one of $R_3$ and $R_4$ represents methyl; (iii) the sum of the carbon atoms in $R_1$, $R_2$, $R_3$, $R_4$ and $R_5$ is 3; and (iv) $R_1$ and $R_2$ represent hydrogen when $R_5$ is methyl.

"Di-isoamylene" is indicated to be synthesized in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

United Kingdom Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as, sulfuric acid or boron trifluoride methyletherate It is further indicated that such compounds are useful intermediates in the production of perfumery compounds. Apparently however, the more volatile di-isoamylenes produced as side-products in the reaction of 2-methyl-butene-2 with alpha-methylstyrene are discarded.

Thus, nothing in the prior art discloses the use of any of the di-isoamylenes of our invention in augmenting or enhancing the aroma of perfume compositions, perfumed articles or colognes.

THE INVENTION

It has now been determined that dimers of isoamylene produced according to the reaction:

are capable of imparting or augmenting or enhancing a variety of fragrances in or to consumable materials.

Briefly, our invention contemplates augmenting or enhancing fragrances of such consumable materials as perfumes, perfumed articles (e.g., solid or liquid anionic, cationic, nonionic or zwitterionic detergents, cosmetic powders, fabric softener compositions and dryer-added fabric softener articles) and colognes by adding thereto, a small, but effective amount of at least one of the compounds defined according to the generic structure:

wherein $R_1$, $R_2$, $R_3$, $R_4$ and $R_5$ represent hydrogen or methyl with the provisos that (i) at least one of $R_1$ and $R_2$ represents methyl (ii) at least one of $R_3$ and $R_4$ represents methyl; (iii) the sum of the carbon atoms in $R_1$, $R_2$, $R_3$, $R_4$ and $R_5$ is 3; and (iv) $R_1$ and $R_2$ represent hydrogen when $R_5$ is methyl.

More specifically, the structures of the compounds useful in practicing our invention are as follows:

The diisoamylene compounds of our invention augment or enhance woody, piney and herbaceous aroma characteristics of perfumes, perfumed articles and colognes, thereby causing one or more of said di-isoamylene compounds to be useful particularly in pine fragrances.

The di-isoamylene derivatives of our invention having the structures:

may be prepared by reacting 2-methyl-2-butene in the presence of an acidic catalyst which may be a Lewis acid such as, zinc chloride, aluminum chloride, aluminum bromide, diethyl aluminum chloride, diethyl aluminum bromide, ethyl aluminum dichloride, and diethyl aluminum bromide, boron trifluoride, boron trifluoride etherate, or any of the other catalysts enumerated in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,638,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

Depending upon the conditions of reaction, including temperature, pressure, mole ratio of 2-methyl-2-butene:-catalyst concentration of 2-methyl-2-butene in solvent, concentration of catalyst in solvent and time of reaction, the ratio and nature of isomers will vary in an as yet undetermined fashion. In any event, this invention contemplates all isomers of di-isoamylene defined according to the structures:

taken alone or in admixture in all proportions, when used in augmenting or enhancing the aroma of perfume compositions, perfumed articles, and colognes.

As olfactory agents, the di-isoamylene derivatives, taken alone or in admixture, of our invention can be formulated into, or used as components of a "perfume composition" or can be used as components of a "perfumed article", or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and hydrocarbons other than the di-isoamylene derivatives of our invention which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) top notes which are usually low boiling, fresh-smelling materials.

In perfume compositions, the individual component will contribute its particular olfactory characteristics, but the overall effect of the perfume composition will be the sum of the effects of each of the ingredients and in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the di-isoamylene derivatives of this invention which will be effective in perfume compositions depends on many factors, including the other ingredients, their amounts and the effects which are desired. It has been found that perfume compositions containing as little as 0.05% of the di-isoamylene derivatives of this invention, or even less, can be used to impart an interesting, herbaceous, piney and woody aroma to soaps, liquid or solid anionic, cationic, non-ionic or zwitterionic, detergents, cosmetics, cosmetic pwoders, liquid and solid fabric softeners, dryer-added fabric softener articles (e.g. BOUNCE ® a registered trademark of the Procter & Gamble Company of Cinncinati, Ohio), optical brightener compositions and other products. The amount employed can range up to 70% or even higher, and will depend on considerations of cost, nature of the end product, and the effect desired on the finished product and particular fragrance sought. Thus, for example, when fragrancing liquid bleach compositions containing alkalihypochlorite such as, for example, sodium hypochlorite, for example CLOROX ®, (registered trademark of CLOROX, Inc.). The amount employed can be as high as 100% of the fragrance involved in the liquid bleach. Indeed, a distinctive aspect of our invention is the use of one or more of the di-isoamylene derivatives in a stable liquid bleach composition.

The di-isoamylene derivatives of this invention, taken alone or in admixture, can be used alone, or in a perfume composition as an olfactory component in detergents, soaps, space odorants and deodorants; perfumes; colognes, toilet waters; bath salts; hair preparations, such as lacquers, brillantines, pomades and shampoos; cosmetic preparations, such as creams, deodorants, hand lotions, sunscreens; powders, such as talcs, dusting powders, face powders and the like; liquid bleaches, such as sodium hypochlori—containing bleaches; floor waxes; automobile aromas and automobile polish compositions. When used as an olfactory component of a perfumed article, as little as 0.01% of one or more of the di-isoamylene derivatives, will suffice to impart an interesting, herbaceous, piney and woody aroma. Generally, no more than 0.5% is required to impart such aromas, however, in view of the rather low cost of the di-isoamylene derivatives of our invention, up to 100% of the perfume composition, can be one or more of the di-isoamylene derivatives.

In addition, the perfume composition can contain a vehicle or carrier for the di-isoamylene derivatives, alone, or with other ingredients. The vehicle can be a liquid such as a non-toxic alcohol such as ethanol, a glycol such as propylene glycol, or the like. The carrier can be an absorbent solid, such as a gum or components for encapsulating the composition such as gelatin which can be used to form a capsule wall surrounding the perfume oil, as by means of coacervation.

It will thus be apparent that the di-isoamylene derivatives of our invention can be utilized to alter, modify, augment or enhance sensory properties, particularly organoleptic properties such as fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF DI-ISOAMYLENE DERIVATIVES

Reaction:

Di-isoamylene is prepared according to one of the procedures set forth in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

As an illustration, and not by way of limitation, the following Example sets forth the preparation of di-isoamylenes useful in producing the fragrances of our invention:

Over a period of ten hours, 2-methyl-2-butene is pumped through a 5'×5/8 (0.625 inch) tube packed with 15.0 g of polystyrene sulfonic acid catalyst, at a temperature of 100° C. and at a pressure of 400 psig.

Figure 1A:
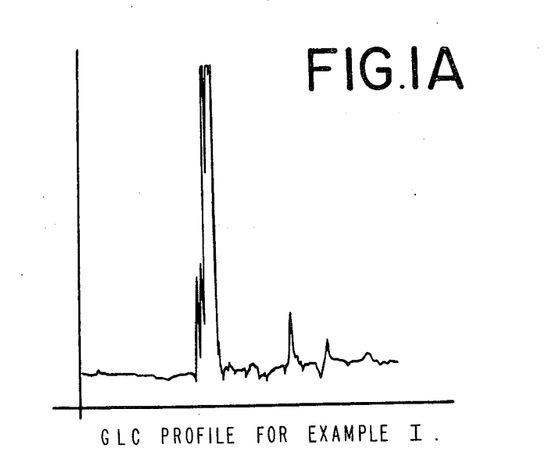
FIG. 1A represents the GLC profile for the reaction product of Example I using a 70% sulfuric acid catalyst at 35° C.

The resulting material was distilled in a fractionation column in order to separate the di-isoamylene from the higher molecular weight polymers, which are formed during the reaction as by-products. FIG. 1A represents the GLC profile for the reaction product of Example I using a 70% sulfuric acid catalyst at 35° C.

Figure 1B:
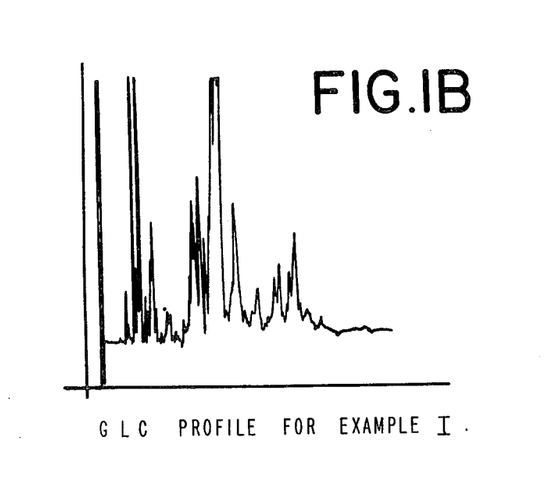
FIG. 1B represents the GLC profile for the reaction product of Example I using an Amberlyst ® 15 acidic ion exchange resin catalyst at a temperature of 150° C.

FIG. 1B represents the GLC profile for the reaction product of Example I using an Amberlyst ® 15 acetic ion exchange resin catalyst at a temperature of 150° C.

Figure 1C:
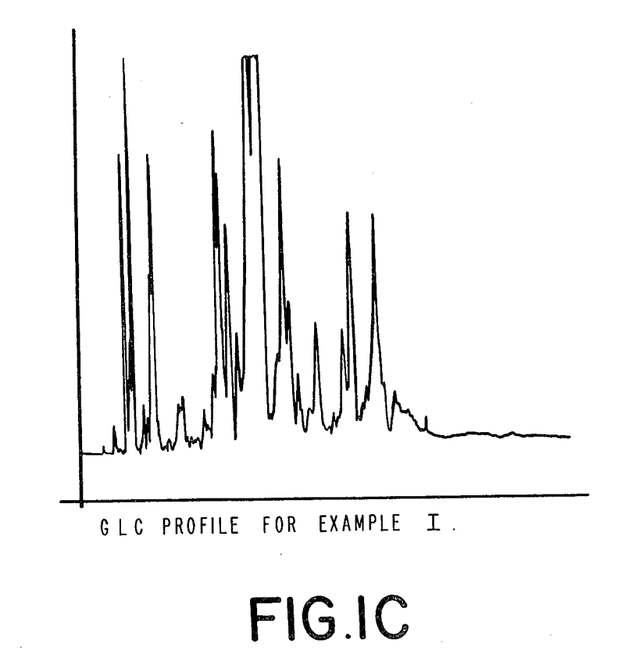
FIG. 1C represents the GLC profile for the reaction product of Example I, using an Amberlyst ® 15 catalyst at 100° C.

FIG. 1C represents the GLC profile for the reaction product of Example I, using an Amberlyst ® 15 catalyst at 100° C.

Figure 1D:
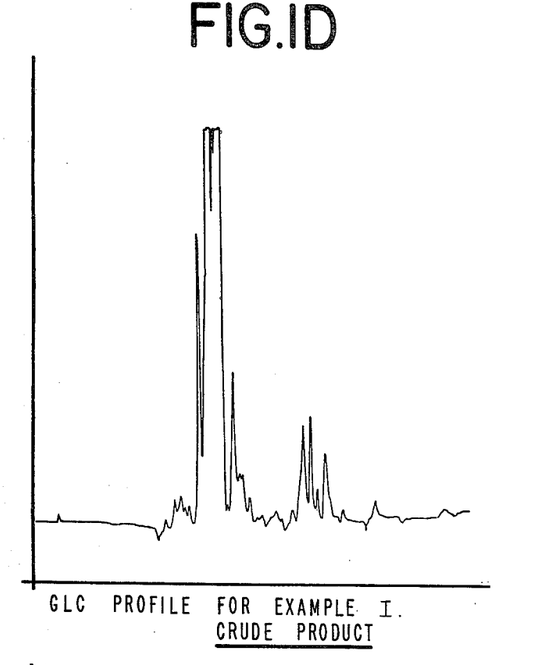
FIG. 1D represents the GLC profile for the reaction product of Example I, using a sulfuric acid catalyst and an alpha-methylstyrene diluent at 35° C. according to the conditions of United Kingdom Patent Specification No. 796,130 (crude reaction product)

FIG. 1D represents the GLC profile for the reaction product of Example I, using a sulfuric acid catalyst and an alpha-methylstyrene diluent at 35° C. according to the conditions of United Kingdom Patent Specification 796,130 (crude reaction product)

Figure 1E:
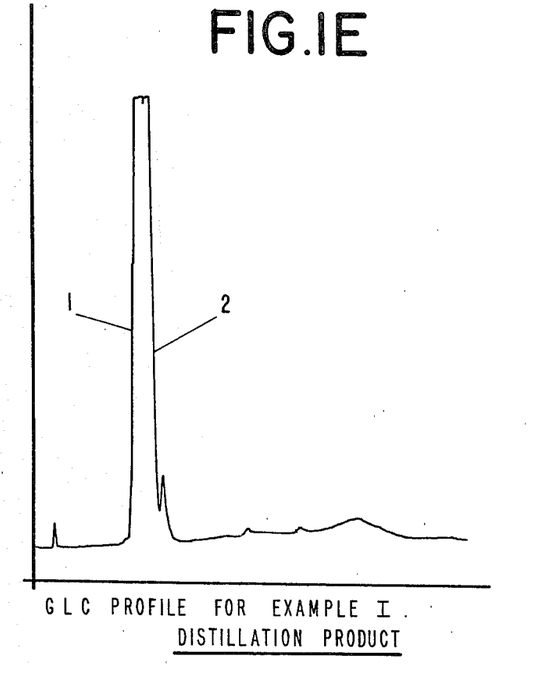
FIG. 1E represents the GLC profile for the reaction product of Example I, using a sulfuric acid catalyst, at 35° C. and an alpha-methylstyrene diluent according to the conditions of United Kingdom Patent Specification No. 796,130 (distilled reaction product).

FIG. 1E represents the GLC profile for the reaction product of Example I, using a sulfuric acid catalyst, at 35° C. and an alpha-methylstyrene diluent according to the conditions of United Kingdom Patent Specification No. 796,130 (distilled reaction product).

Figure 2A:
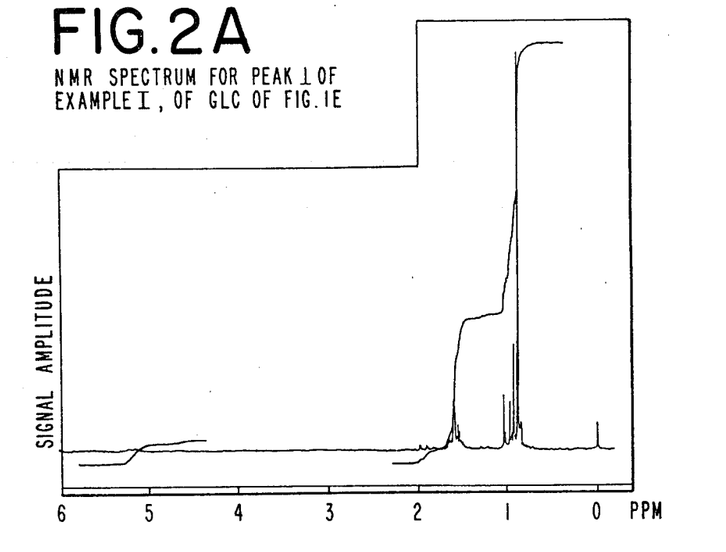
FIG. 2A represents the NMR spectrum for Peak 1 of the GLC profile of FIG. 1E.
Figure 2B:
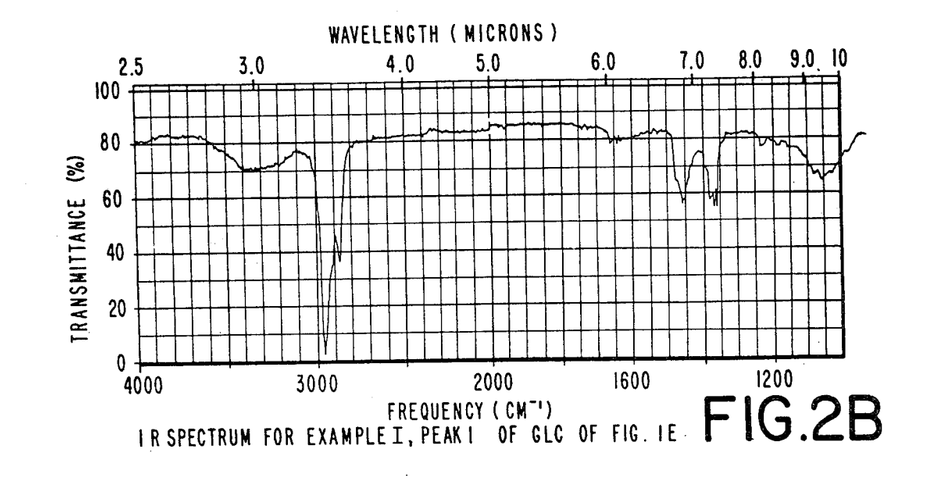
FIG. 2B represents the infra-red spectrum for Peak 1 of the GLC profile of FIG. 1E

FIG. 2A represents the NMR spectrum for Peak 1 of the GLC profile of FIG. 1E. Peak 1 has been determined by analysis to be the compound having the structure:

FIG. 2B represents the infra-red spectrum for Peak 1 of the GLC profile of FIG. 1E.

Figure 3A:
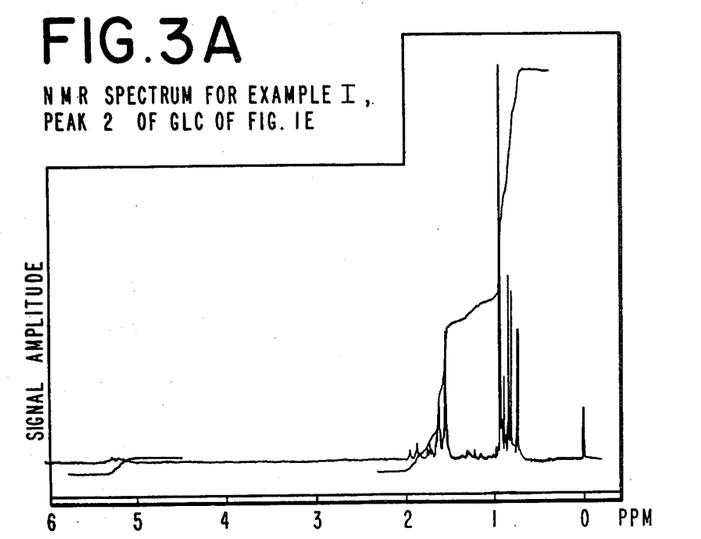
FIG. 3A represents the NMR spectrum for Peak 2 of the GLC profile of FIG. 1E.
Figure 3B:
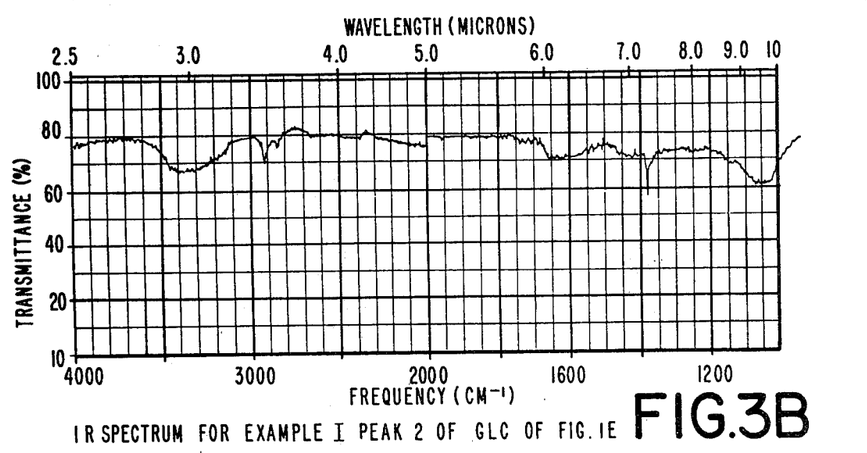
FIG. 3B represents the infra-red spectrum for Peak 2 of the GLC profile of FIG. 1E.

FIG. 3A represents the NMR spectrum for Peak 2 of the GLC profile of FIG. 1E. Peak 2 contains compounds having the structures:

FIG. 3B represents the infra-red spectrum for Peak 2 of the GLC profile of FIG. 1E.

Figure 4:
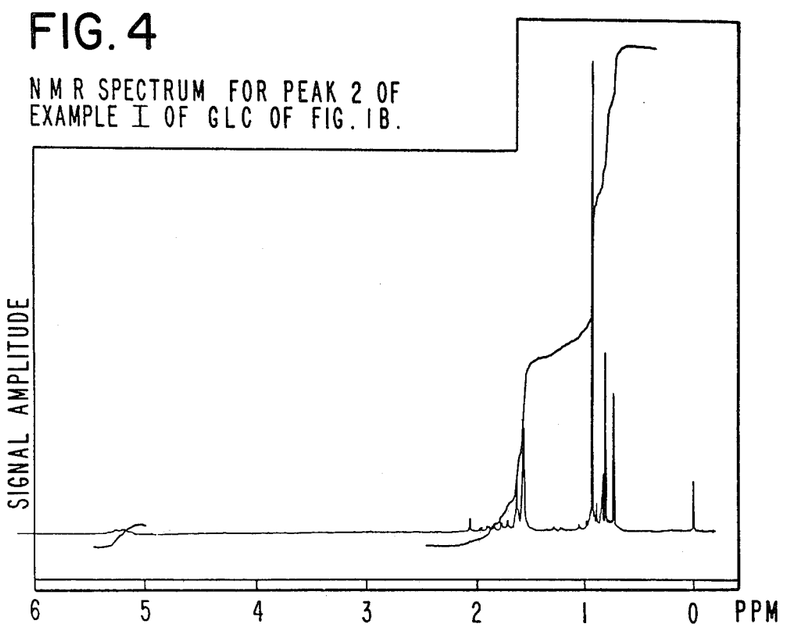
FIG. 4 represents the NMR spectrum for Peak 2 of the GLC profile of FIG. 1B.

FIG. 4 represents the NMR spectrum for Peak 2 of the GLC profile of FIG. 1B.

EXAMPLE II

The di-isoamylene produced according to Example I has a woody, piney, herbaceous note which may be utilized to a great extent in inexpensive functional products. The following pine fragrance demonstrates the use of this material in perfume compositions. In this case it is used as 47.9%.

| | |
|---|---|
| Di-isoamylene | 479 |
| Isobornyl Acetate | 100 |
| Camphor | 10 |
| Terpineol | 25 |
| Fir Balsam Absolute (50% in Diethyl Phthalate | 20 |
| Coumarin | 4 |
| Linalool | 30 |
| Anethol | 2 |
| Fenchyl Alcohol | 10 |
| Lemon Terpenes Washed | 50 |
| Borneol | 5 |
| Galbanum Oil | 5 |
| Turpentine Russian | 150 |
| Pinus Pumilionus | 50 |
| Eucalyptol | 50 |
| 2,2,6-trimethyl-1-cyclohexene-1-carboxaldehyde | 5 |
| Maltol 1% in Diethyl Phthalate | 5 |

The presence of the di-isoamylene supports the pine notes and produces a considerable savings in the cost of the formulation.

EXAMPLE III

PREPARATION OF A COSMETIC POWDER COMPOSITION

A cosmetic powder is prepared by mixing in a ball mill, 100 g of talcum powder with 0.25 g of the perfume composition prepared according to Example II. It has an excellent, piney aroma with woody and herbaceous nuances.

EXAMPLE IV

PERFUMED LIQUID DETERGENT

Concentrated liquid detergents (Lysine salt of n-dodecylbenzene sulfonic acid as more specifically described in U.S. Pat. No. 3,948,818, issued on April 6, 1976) with herbaceous, woody and piney aroma nuances are prepared containing 0.10%, 0.15%, 0.20%, 0.25%, 0.30% and 0.35% of the fragrance prepared according to Example II. They are prepared by adding and homogeneously mixing the appropriate quantity of fragrance formulation prepared according to Example II in the liquid detergent. The detergents all possess excellent piney aromas with woody and herbaceous undertones, the intensity increasing with greater concentrations of perfume composition of Example II.

EXAMPLE V

PREPARATION OF A COLOGNE AND HANDKERCHIEF PERFUME

The composition prepared according to Example II is incorporated into a cologne at concentrations of 2.0%, 2.5%, 3.0%, 3.5%, 4.0%, 4.5% and 5.0% in 85% aqueous food grade ethanol; and into a handkerchief perfume at concentrations of 15%, 20%, 25% and 30% (in 95% aqueous food grade ethanol). A distinctive and definite herbaceous, woody, piney aroma is imparted to the cologne and to the handkerchief perfume at all levels indicated above.

EXAMPLE VI

PREPARATION OF SOAP COMPOSITION

One hundred grams of soap chips (IVORY ®, produced by the Procter & Gamble Company, Cinncinati, Ohio) are mixed with one gram of the formulation of Example II until homogeneous compositions are obtained. In each of the cases, the homogeneous compositions are heated under three atmospheric pressure at 180° C. for a period of three hours and the resulting liquids are placed into soap molds. The resulting soap cakes, on cooling, manifest excellent herbaceous, woody and piney aromas with an emphasis on the piney aspects of the aroma.

EXAMPLE VII

PREPARATION OF A SOLID DETERGENT COMPOSITION

A detergent is prepared from the following ingredients according to Example 1 of Canadian No. Pat. No. 1,007,948:

| Ingredient | Percent by Weight |
| --- | --- |
| "Neodol ® 45-11 (a $C_{14}$–$C_{15}$ Alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.10, 0.15, 0.20 and 0.25 grams of the pine perfume of Example II. The detergent sample has an excellent herbaceous, woody and piney aroma.

EXAMPLE VIII

PREPARATION OF A COSMETIC POWDER COMPOSITION

A cosmetic powder is prepared by admixing in a ball mill, 100 g of talcum powder with 0.25 g of one of the di-isoamylene compounds prepared according to Example I. The resulting cosmetic powder has an excellent herbaceous, piney and woody aroma.

EXAMPLE IX

PERFUMED LIQUID DETERGENT

Concentrated liquid detergents (Lysine salt of n-dodecylbenzene sulfonic acid as more specifically described in U.S. Pat. No. 3,948,818, issued on April 6, 1976) with herbaceous, woody and piney aroma notes are prepared containing 0.10%, 0.15%, 0.20% and 0.25% of one or more of the di-isoamylenes prepared according to Example I. They are prepared by adding and homogeneously mixing the appropriate quantity of di-isoamylene composition in the liquid detergent. The detergents all possess piney, woody and herbaceous nuances, the intensity of each characteristic increasing with greater concentrations of di-isoamylene composition of Example I.

EXAMPLE X

PREPARATION OF COLOGNES AND HANDKERCHIEF PERFUMES

The di-isoamylene derivatives prepared according to Example I are incorporated into colognes at concentrations of 2.0%, 2.5%, 3.0%, 3.5%, 4.0% and 4.5% in 85% aqueous food grade ethanol; and into handkerchief perfumes at concentrations of 15%, 20%, 25% and 30% (in 95% aqueous ethanol). Distinctive herbaceous, woody and piney nuances are imparted to the colognes and to the handkerchief perfumes at various levels indicated above.

EXAMPLE XI

Utilizing the procedure of Example I of column 15 of U.S. Pat. No. 3,632,396, a nonwoven cloth substrate useful as a dryer-added fabric-softening article of manufacture prepared wherein the substrate, the substrate coating and the outer coating and the perfuming material are as follows:

1. a water "dissolvable" paper ("Dissolvo Paper").
2. Adogen 448 (m.p. about 140° F.) as the substrate coating; and
3. An outer coating having the following formulation (m.p. about 150° F.):
   57 percent $C_{20-22}$ HAPS
   22 percent isopropyl alcohol
   20 percent antistatic agent
   1 percent of one or more of the di-isoamylene derivatives of Example I.

Fabric-softening compositions prepared according to Example I having woody, piney and herbaceous aroma characteristics essentially consist of a substrate having a weight of about 3 grams per 100 square inches of substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The woody, herbaceous and piney aroma is imparted in a pleasant manner to the head space in the dryer on operation thereof, using the said dryer-added fabric softening nonwoven fabric.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of AKZO of Chicago, Illinois.

EXAMPLE XII

Four drops of one of the di-isoamylene compositions prepared according to Example I is added to two grams of Aromox ® DMC-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody/piney/herbaceous" aroma. Furthermore, no such characteristic "hypochlorite" aroma is retained on the hands of the individual handling such laundry in both the wet and the dry states.

EXAMPLE XIII

Aromox ® DMMC-W in various quantities is mixed with 0.1 gram of one of the di-isoamylene compositions prepared according to Exampe 1. The resulting premixes are then added to 200 grams of an aqueous 5% sodium hypochlorite solution. Sufficient 12.5 M aqueous NaOH is added to bring the pH of the mixture up to 13. The following results are obtained.

| Percentage Aromox DMMC-W | Clarity of hypochlorite solution after addition of premix |
| --- | --- |
| 0.23% | Clear after three days |
| 0.15% | Clear after three days |
| 0.08% | Initially slightly turbid; two phases exist after three days. |

EXAMPLE XIV

Two grams of Aromox ® DMMC-W is admixed with eight drops of one of the di-isoamylene compositions of Example I. The premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry on dry-out in an atmosphere of 50% relative humidity retains a "clean fresh" woody, herbaceous, piney aroma; whereas without the use of the di-isoamylene prepared according to Example I, the bleached laundry has a faint characteristic disagreeable "hypochlorite" aroma.

EXAMPLE XV

Two grams of Aromox ® DMMC-W is admixed with eight drops of one of the di-isoamylene compositions of Example I. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh", woody, herbaceous, piney aroma; whereas without the use of the di-isoamylene prepared according to Example I, the bleached laundry has a faint characteristic disagreeable "hypochlorite" aroma.

EXAMPLE XVI

Two grams of Aromox ® DMMC-W is admixed with eight drops of one of the di-isoamylene products produced according to Example I. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity, retains a "woody, herbaceous, piney" aroma whereas without the use of the di-isoamylene composition of Example I, the bleached laundry has a faint characteristic disagreeable "hypochlorite" aroma.

EXAMPLE XVII

Four drops of one of the di-isoamylene mixtures produced according to Example I, is added to 1.5 grams of Aromox ® NCMDW to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XVIII

Four drops of one of the di-isoamylene mixtures produced according to Example I, is added to 1 gram n-undecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XIX

Four drops of one of the di-isoamylene mixtures produced according to Example I is added to 1 gram of n-dodecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XX

One gram of n-tridecyl dimethyl amine oxide is admixed with eight drops of one of the di-isoamylene compositions of Example I. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "clean fresh, woody, herbaceous, piney" aroma; whereas without the use of one of the di-isoamylene compositions of Example I, the bleached laundry has a faint characteristic disagreeable "hypochlorite" aroma.

What is claimed is:

1. A process for augmenting or enhancing the aroma of a liquid bleach containing a hypochlorite ion comprising the step of adding to a hypochlorite ion containing bleach an aroma augmenting or enhancing quantity of one or more diisoamylene compositions produced by the step of reacting two moles of isoamylene in the presence of an acid catalyst, the resulting diisoamylene containing composition being defined according to the generic structure:

wherein $R_1$, $R_2$, $R_3$, $R_4$ and $R_5$ each represent hydrogen or methyl with the provisos that (i) at least one of $R_1$ or $R_4$ represents methyl;
(ii) the sum of the carbon atoms in $R_1$, $R_2$, $R_3$, $R_4$ and $R_5$ is 3; and
(iii) $R_1$ and $R_2$ are each hydrogen when $R_5$ is methyl.

* * * * *